US006522932B1

(12) United States Patent
Kuzma et al.

(10) Patent No.: US 6,522,932 B1
(45) Date of Patent: Feb. 18, 2003

(54) IMPLANTABLE, EXPANDABLE, MULTICONTACT ELECTRODES AND TOOLS FOR USE THEREWITH

(75) Inventors: Janusz A. Kuzma, Englewood, CO (US); Carla M. Mann, Los Angeles, CA (US)

(73) Assignee: Advanced Bionics Corporation, Sylmar, CA (US)

(*) Notice: Subject to any disclaimer, the term of this patent is extended or adjusted under 35 U.S.C. 154(b) by 49 days.

(21) Appl. No.: 09/783,237

(22) Filed: Feb. 13, 2001

Related U.S. Application Data

(63) Continuation-in-part of application No. 09/239,927, filed on Jan. 28, 1999, now Pat. No. 6,205,361.
(60) Provisional application No. 60/074,198, filed on Feb. 10, 1998.

(51) Int. Cl.[7] .................................................. A61N 1/05
(52) U.S. Cl. ....................................... 607/116; 607/117
(58) Field of Search ............................... 607/115, 116, 607/117, 152; 600/373, 374, 377

(56) References Cited

U.S. PATENT DOCUMENTS

| 3,724,467 A | 4/1973 | Avery et al. ................ 128/418 |
| 4,141,365 A | 2/1979 | Borkan et al. .............. 128/404 |
| 4,166,469 A | 9/1979 | Littleford .................... 128/784 |
| 4,379,462 A | 4/1983 | Borkan et al. .............. 128/786 |
| 4,512,351 A * | 4/1985 | Pohndorf ..................... 128/786 |
| 4,989,617 A | 2/1991 | Memberg et al. .......... 128/785 |
| 5,143,067 A | 9/1992 | Rise et al. ................... 128/642 |
| 5,282,468 A | 2/1994 | Klepinski .................... 128/642 |
| 5,391,200 A | 2/1995 | KenKnight et al. ......... 607/129 |
| 5,397,342 A | 3/1995 | Heil, Jr. et al. ............. 607/129 |
| 5,417,719 A | 5/1995 | Hull et al. .................... 607/46 |
| 5,458,629 A | 10/1995 | Baudino et al. ............. 607/116 |
| 5,634,462 A | 6/1997 | Tyler et al. .................. 128/642 |
| 5,643,330 A | 7/1997 | Holsheimer et al. .......... 607/46 |
| 5,733,322 A | 3/1998 | Starkebaum ................. 607/117 |
| 6,205,361 B1 | 3/2001 | Kuzma et al. ............... 607/117 |
| 6,309,401 B1 | 10/2001 | Redko et al. ................ 606/185 |

FOREIGN PATENT DOCUMENTS

EP          1048270          1/2000

* cited by examiner

*Primary Examiner*—Gregory Wilson
(74) *Attorney, Agent, or Firm*—Laura Haburay Bishop; Bryant R. Gold

(57) ABSTRACT

A paddle-type electrode or electrode array is implantable like a percutaneously inserted lead, i.e., without requiring major surgery, and once implanted, expands to provide a platform for many electrode configurations. The electrode array is provided on a flexible, foldable, subcarrier or substrate. Such subcarrier or substrate folds or compresses during implantation, thereby facilitating its insertion using percutaneous implantation techniques and tools. Once implanted, such subcarrier or substrate expands, thereby placing the electrodes in a desired spaced-apart positional relationship, and thus achieving a desired electrode array configuration. A steering stylet may be accommodated in a lumen provided in the subcarrier or substrate. Insertion tools useful with such electrode arrays include a needle with an oblong cross-section, which accommodates the dimensions of the folded array, and also accommodates other electrode arrays that are not necessarily folded.

24 Claims, 16 Drawing Sheets

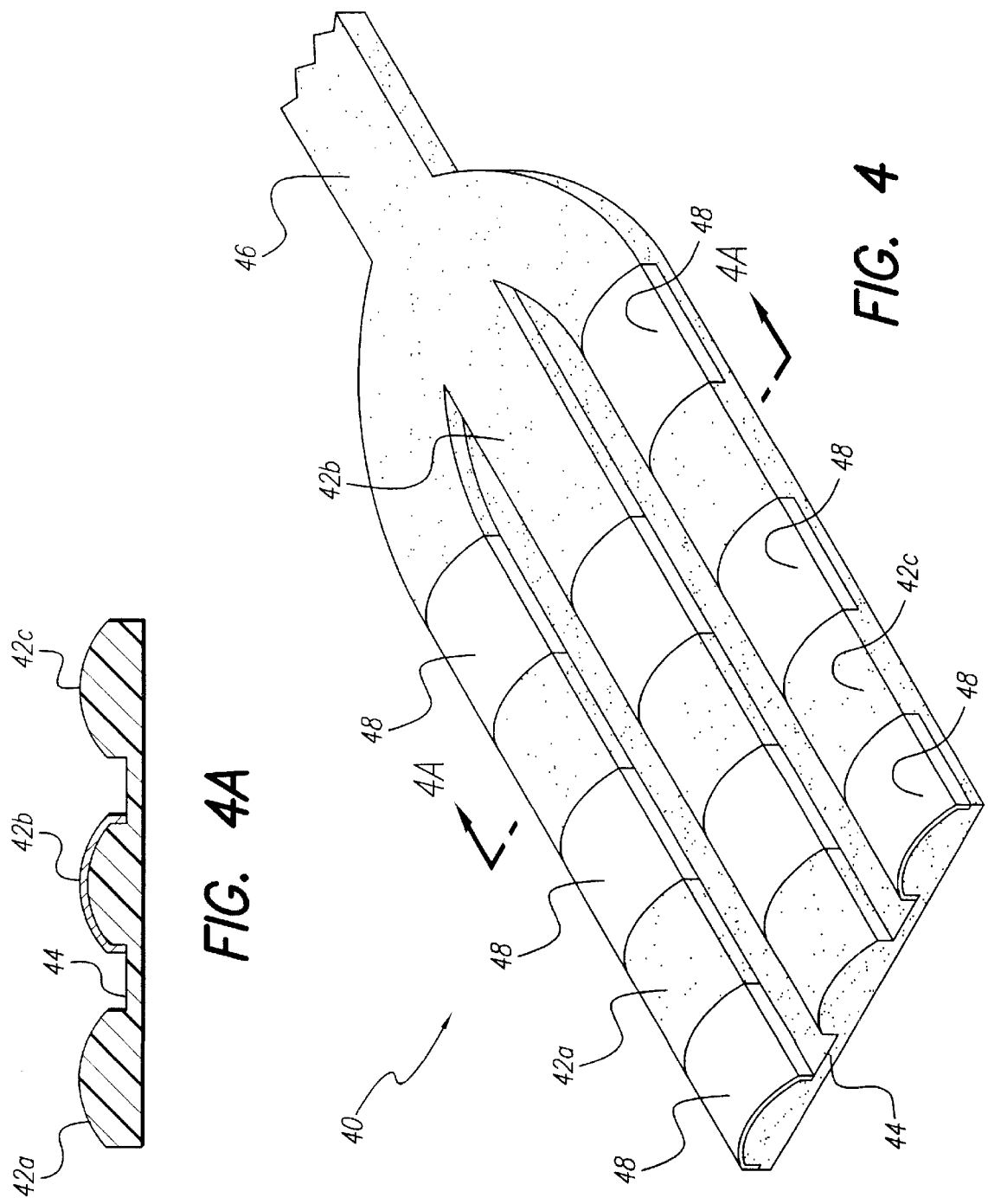

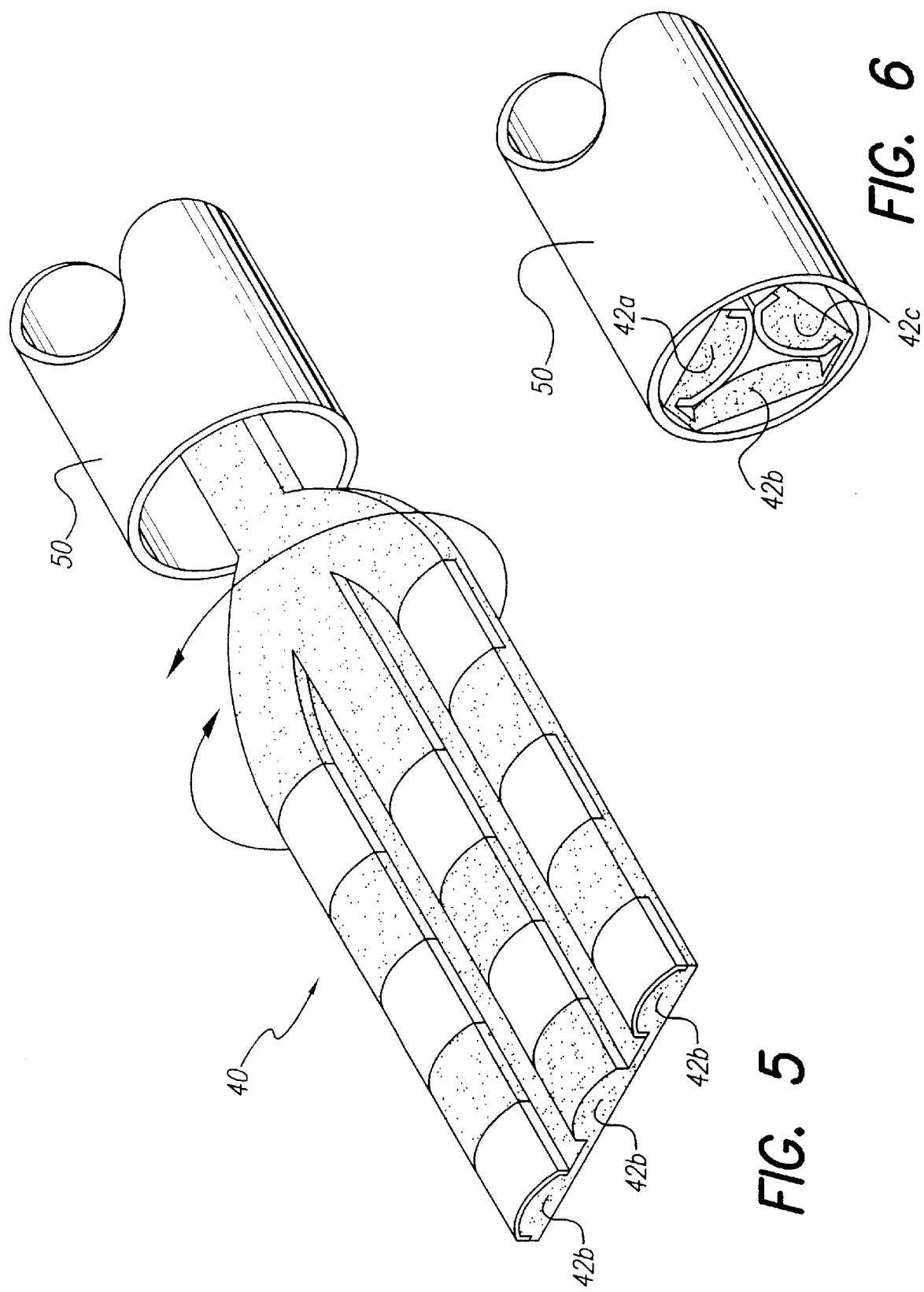

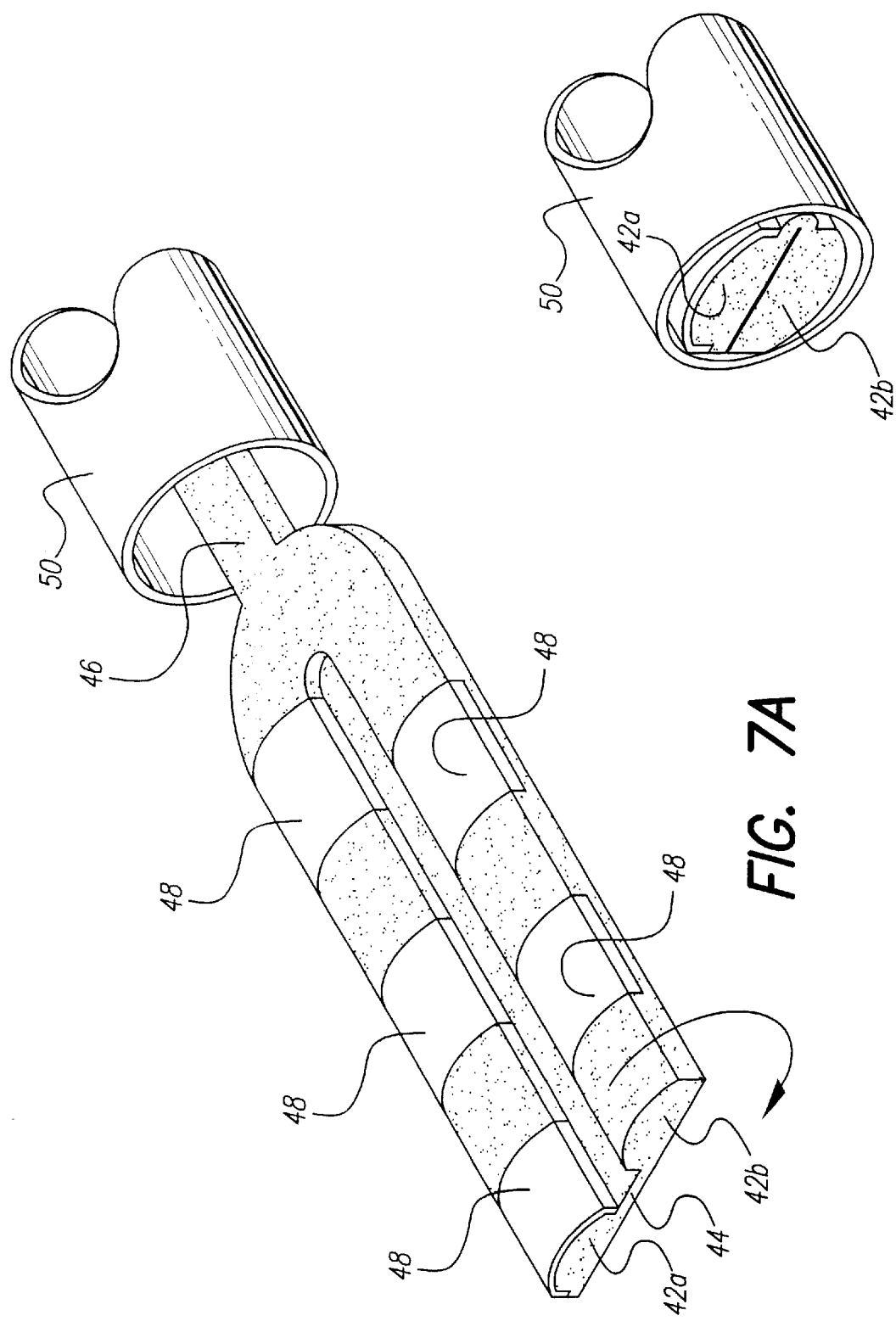

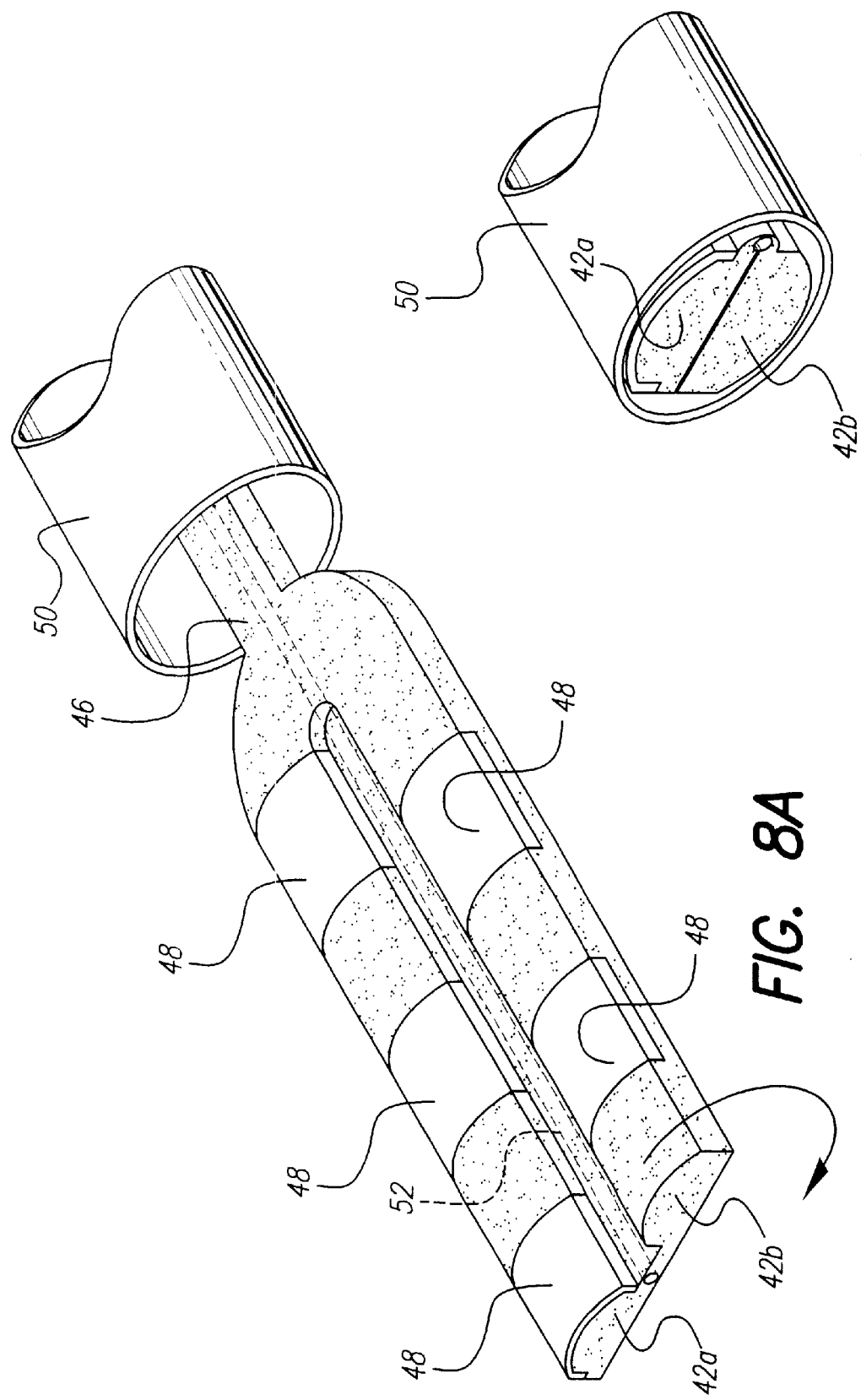

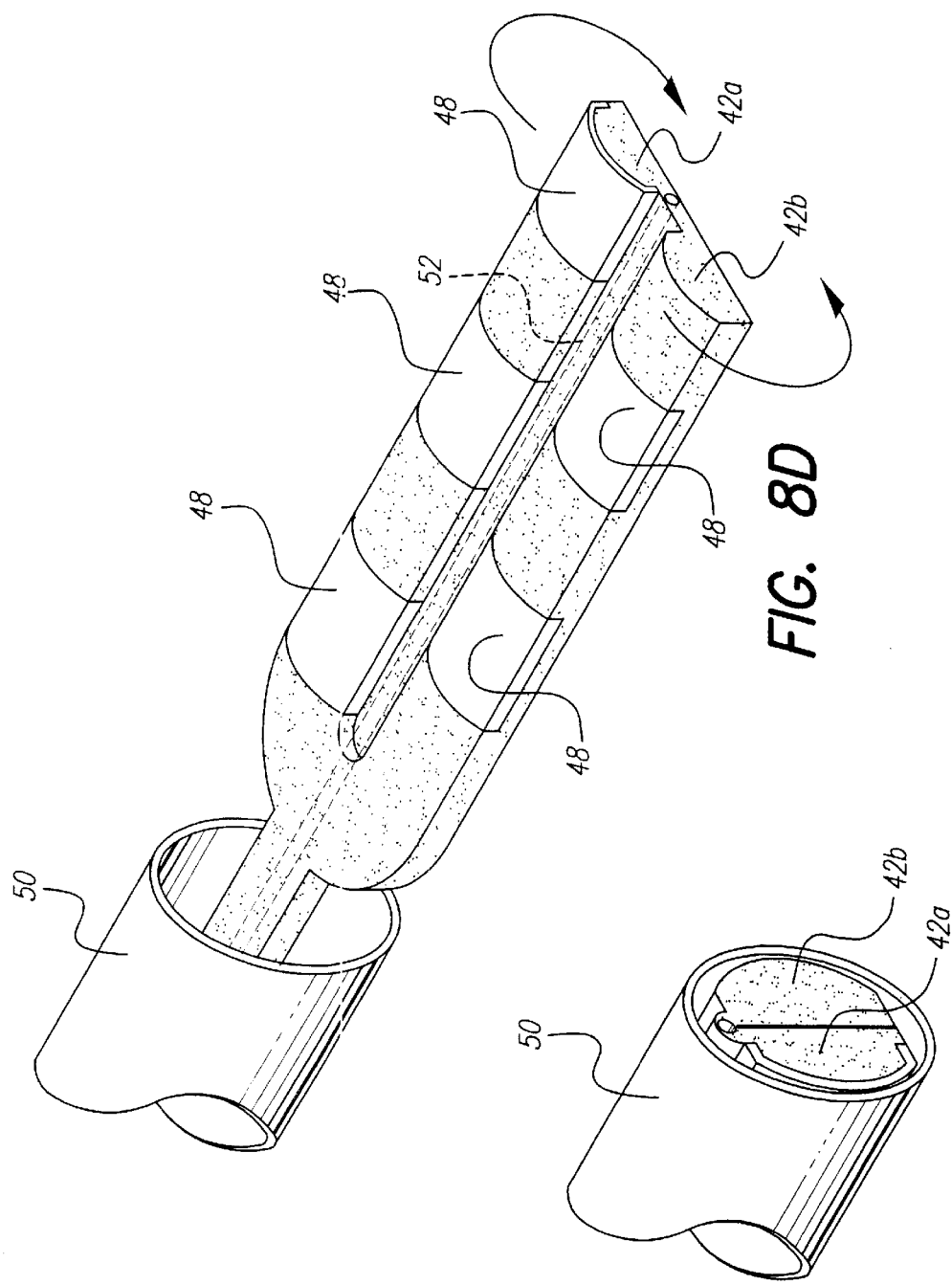

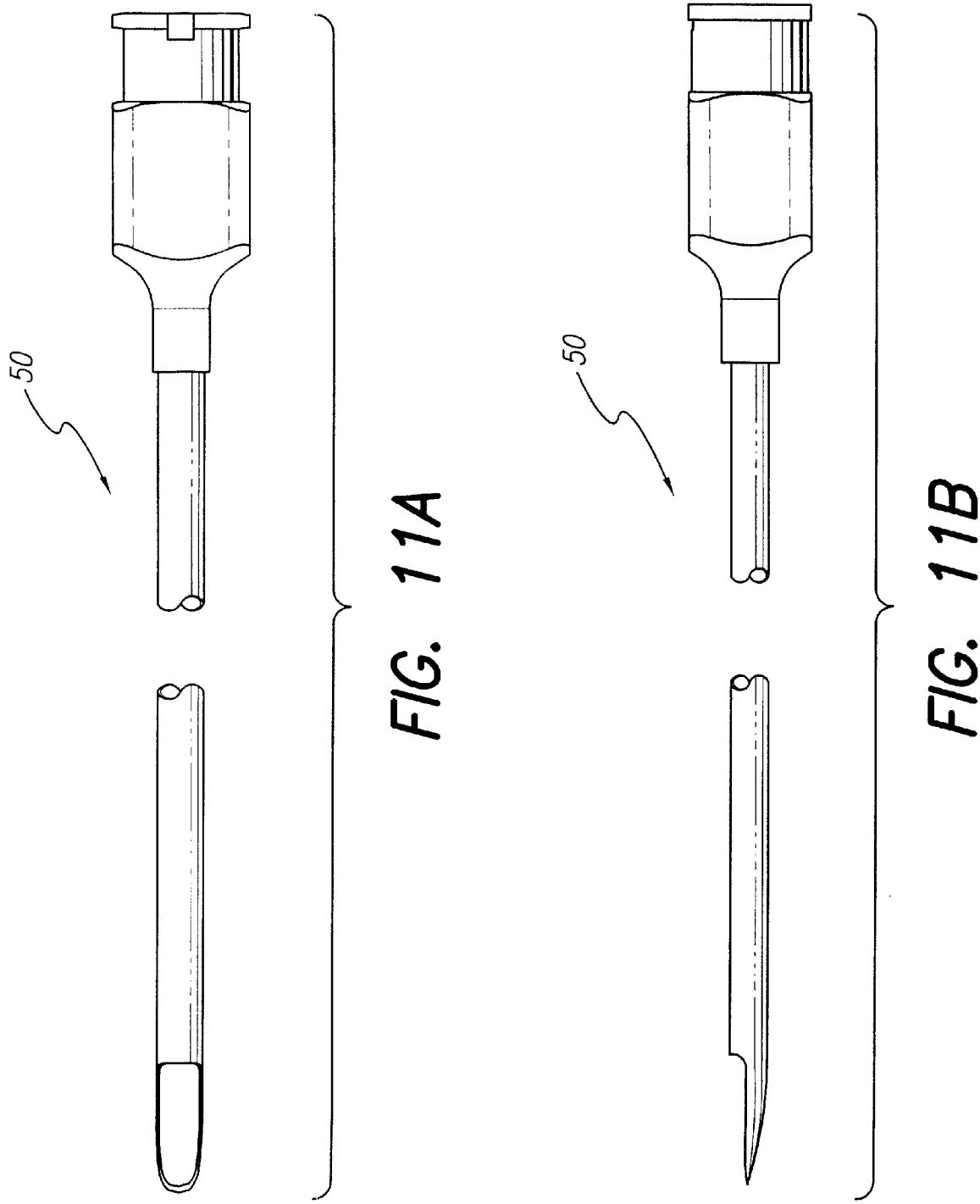

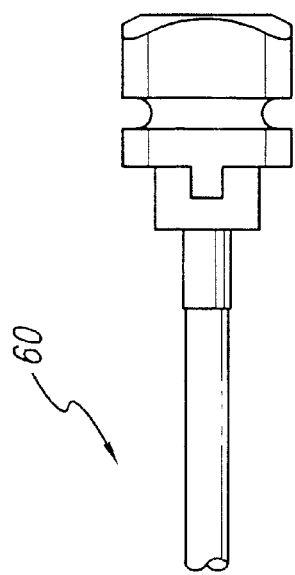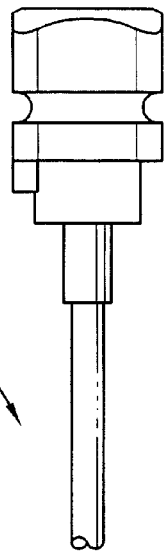
FIG. 12A
FIG. 12B

IMPLANTABLE, EXPANDABLE, MULTICONTACT ELECTRODES AND TOOLS FOR USE THEREWITH This application is a continuation-in-part of U.S. patent application Ser. No. 09/239,927, filed Jan. 28, 1999, now U.S. Pat. No. 6,205,361 which in turn claims the benefit of U.S. Provisional Application Ser. No. 60/074,198, filed Feb. 10, 1998.

BACKGROUND OF THE INVENTION

The present invention relates to implantable, expandable, multicontact electrodes and tools used for their placement. In a preferred embodiment, such electrodes comprise deployable, paddle-type, multicontact electrodes useful for spinal stimulation.

There are two major types of electrodes used for spinal stimulation: (1) percutaneously implanted in-line electrodes/leads requiring local anesthesia for implant, and (2) paddle-shaped electrodes requiring major surgery for implantation.

The first type of electrodes, i.e., the in-line electrodes, comprise thin, rod-type electrodes. Such in-line or rod-type electrodes are easy and less invasive to implant, typically requiring only local anesthesia and the use of a large gauge needle. Disadvantageously, such in-line electrodes are not as stable as paddle leads, and are prone to migration.

The second type of electrodes, i.e., the paddle-shaped electrodes, provide a large-area electrode surface to contact the body tissue, much like a miniature ping-pong paddle. Advantageously, such paddle-type electrodes are more effective and stable than in-line electrodes. Moreover, such paddle-type electrodes provide a platform for multiple electrodes in many possible configurations to thereby optimize electrode programming and clinical results. In contrast, the percutaneous in-line electrodes can only combine electrodes in a vertical row. Disadvantageously, however, the paddle-type electrodes require complex major surgery for implantation, along with all the attendant risks associated with major complex surgery.

It is thus evident, that there is a need in the art for an electrode which can deliver the maximum advantages of the paddle-type electrodes, but without requiring extensive surgery for implantation.

SUMMARY OF THE INVENTION

The present invention addresses the above and other needs by combining the advantages of both the paddle-type electrode and the in-line (rod-type) electrode. That is, the present invention provides an implantable electrode or electrode array that may be implanted like a percutaneously inserted lead, i.e., without requiring major surgery, but once inserted, expands to provide a platform for many electrode configurations.

In accordance with one important aspect of the invention, an electrode array is provided on a flexible, foldable, subcarrier or substrate. Such subcarrier or substrate is folded, or compressed during implantation, thereby facilitating its insertion using percutaneous implantation techniques and tools of the present invention. Once implanted, such subcarrier or substrate expands, thereby placing the electrodes in a desired spaced-apart positional relationship, and thus achieving a desired electrode array configuration.

In accordance with another aspect of the invention, the substrate or subcarrier of the electrode array includes a memory element which causes the electrode array to expand or unfold to a desired configuration after the electrode array has been implanted while in a folded up or compressed state.

In accordance with yet another aspect of the invention, the electrode array includes a membrane as an integral part thereof that prevents ingrowth of tissue inside the electrode array, thereby facilitating repositioning, removal, and/or reinsertion of the electrode array, as required.

In one embodiment, the invention may be characterized as a system for implanting an expandable electrode array. Such system includes an electrode array and an insertion tool. The electrode array comprises (a) a flexible substrate, (b) a plurality of substantially parallel columns (which may be consider by some to be rows) of spaced-apart electrodes integrally formed on a surface of the flexible substrate, and (c) means for making electrical contact with each electrode in each of the plurality of substantially parallel columns of electrodes. The flexible substrate normally assumes a substantially planar, flat shape, but is configured so that it may be collapsed or folded so as to assume a folded or compressed state. The insertion tool comprises a hollow tube or hollow needle wherein the electrode array may be placed while in its folded or compressed state.

In order to implant the electrode array, the hollow tube or needle (with the folded or compressed electrode array therein) is injected into the living tissue of the desired implant site. The folded electrode array is then expelled from the hollow tube and allowed to assume its expanded or unfolded state within the tissue.

It is thus a feature of the present invention to provide a foldable, paddle-type electrode which can be implanted using a simple, needle-type tool without major surgical intervention.

It is a further feature of the invention to provide a loading tool that assists with the folding and inserting of the paddle-type electrode into an insertion tool.

It is yet another feature of the invention to provide a simple method of implanting a foldable, paddle-type electrode that does not require major surgical intervention.

BRIEF DESCRIPTION OF THE DRAWINGS

The above and other aspects, features and advantages of the present invention will be more apparent from the following more particular description thereof, presented in conjunction with the following drawings wherein:

FIG. 1A is a sectional view of the electrode array of FIG. 1 taken along the line 1A—1A of FIG. 1;

FIG. 1B is a partial sectional view of the electrode array of FIG. 1 taken along the line 1B—1B of FIG. 1;

FIG. 4 illustrates an alternative embodiment of an implantable, foldable electrode array made in accordance with the invention;

FIG. 4A is a sectional view of the electrode array of FIG. 4 taken through the line 4A—4A in FIG. 4;

FIG. 5 shows the manner in which the electrode array of FIG. 4 is folded in order to fit within the lumen of an insertion tool;

FIG. 6 illustrates the folded electrode array of FIGS. 4 and 5 inside of the lumen of an insertion tool;

FIG. 7A shows an alternative implantable, foldable electrode array, and a manner of folding the array to fit within the lumen of an insertion tool;

FIG. 7C illustrates the folded electrode array of either FIG. 7A or FIG. 7B inside the lumen of an insertion tool;

FIG. 8A shows another alternative implantable, foldable electrode array including a lumen for a stylet, and a manner of folding the array to fit within the lumen of an insertion tool;

FIG. 8C illustrates the folded electrode array of FIG. 8A inside the lumen of an insertion tool;

FIG. 8D shows alternative manner of folding the array of FIG. 8A to fit within the lumen of an insertion tool;

FIG. 8E illustrates the folded electrode array of FIG. 8D inside the lumen of an insertion tool;

FIG. 11A illustrates a top view of an insertion tool of the present invention;

FIG. 11B illustrates a side view of the insertion tool of FIG. 11A;

FIG. 12A illustrates a top view of a stylet for use with the insertion tool of FIG. 11A;

FIG. 12B illustrates a side view of the stylet of FIG. 12A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
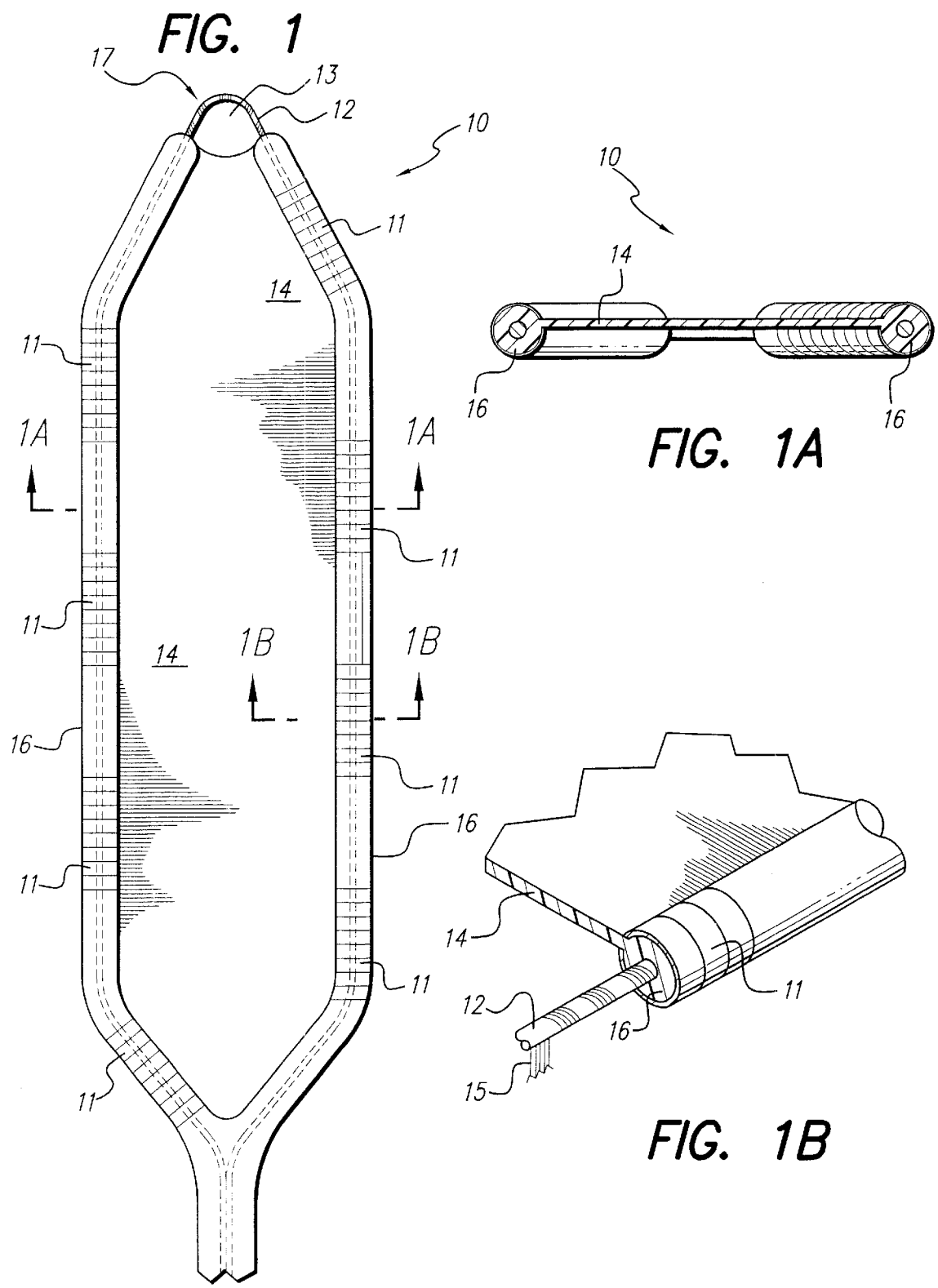
FIG. 1 shows a planar view of an implantable, foldable, collapsible electrode array made in accordance with one embodiment of the invention.

Referring first to FIGS. 1, 1A and 1B, there is shown respectively a planar view of one embodiment of an implantable, foldable, collapsible electrode array 10 made in accordance with the invention, a sectional view of the electrode array 10 taken along the line 1A—1A, and a partial sectional view of the electrode array 10 taken along the line 1B—1B. As can be seen in these figures, the electrode array 10 is made in the form of a paddle having a number of electrode contacts 11 arranged along two substantially parallel columns of a cylindrical edge portion 16 of the electrode array 10. The electrode contacts 11 are spaced apart from each other, and each is electrically connected to a conductive wire(s) 15 that passes through, or is embedded within, the cylindrical edge portion 16 of the array 10.

The electrode contacts 11 may be made, e.g., from a coiled metal foil or clamped as C-shaped metal preforms. As seen best in FIG. 1B, the wires 15 that are electrically connected to the electrode contacts 11 are typically wound around a shape-memory element 12 that passes through the center of the cylindrical edge portions 16 of the array 10.

As indicated, the memory element 12 is placed in the center of the cylindrical edge portion 16. This memory element is selected to have a shape that maintains the open, paddle shape of the electrode array 10 as shown in FIG. 1. The shape-memory element 12 may be made from either metal or from a polymer, such as nylon. The memory element 12 is flexible or resilient, so that it can be folded or bent to another shape, as desired or needed, but in the absence of an external folding or bending force, assumes the open, paddle shape shown in FIG. 1.

The space between the cylindrical edge portions 16 of the paddle array 10 is filled with a thin web or membrane 14 made, e.g., from a suitable flexible non-conductive material such as silicone or other implantable lead materials, as is known in the art. Such membrane advantageously prevents tissue ingrowth within the electrode array 10 after implant, thereby making it possible (when needed) to explant the electrode, or to reposition the electrode with minimal trauma to the patient.

At a distal tip 17 of the array 10 of one embodiment of the invention, the thin membrane 14 and the cylindrical edge portions 16 terminate so as to expose the memory shape element 12 at the distal tip, thereby forming an attachment loop 13. This attachment loop 13 is used during the implant operation of the electrode of one embodiment, as explained more fully below.

In one embodiment of the invention, the width of the paddle electrode array 10 of the type shown in FIG. 1, when maintained in its extended or full paddle shape as shown in FIG. 1, is approximately 10 mm, and has a length of about 45 mm. The diameter of the cylindrical edge portions is approximately 1.2 mm, and the thickness of the membrane 14 is about 0.2 mm.

Figure 2:
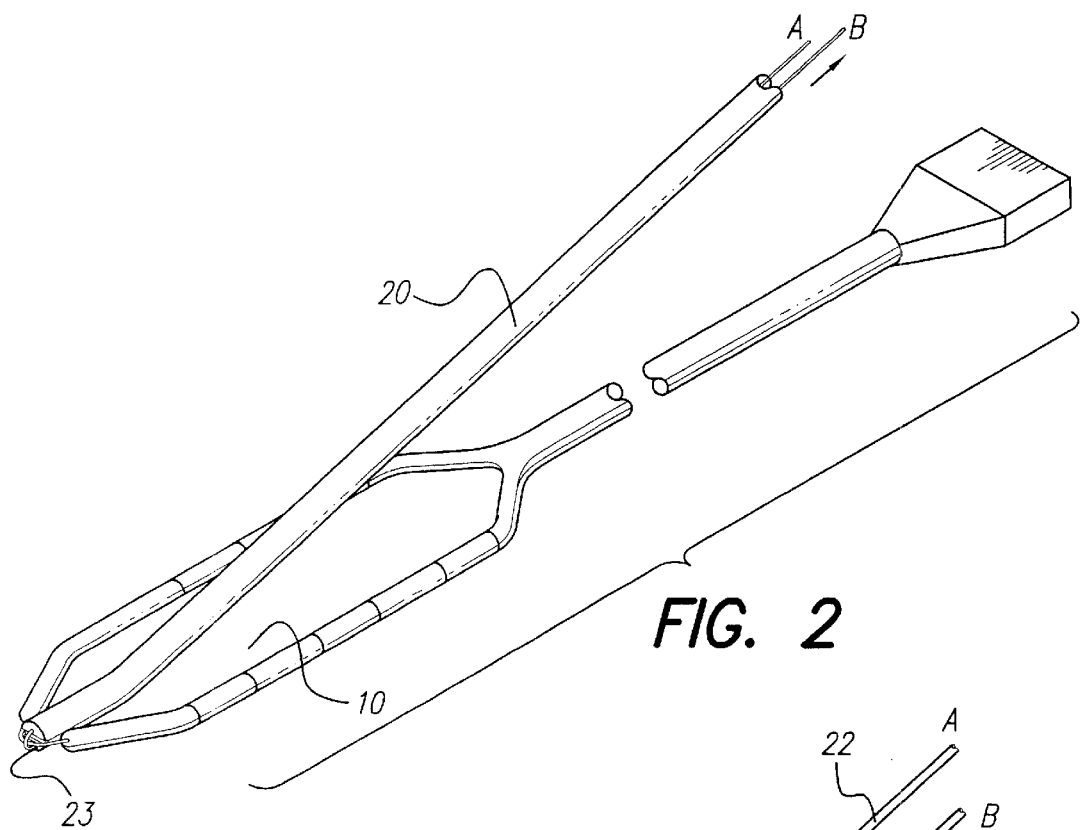
FIG. 2 illustrates one manner in which the electrode array of FIG. 1 may be implanted using an insertion stylet.
Figure 2A:
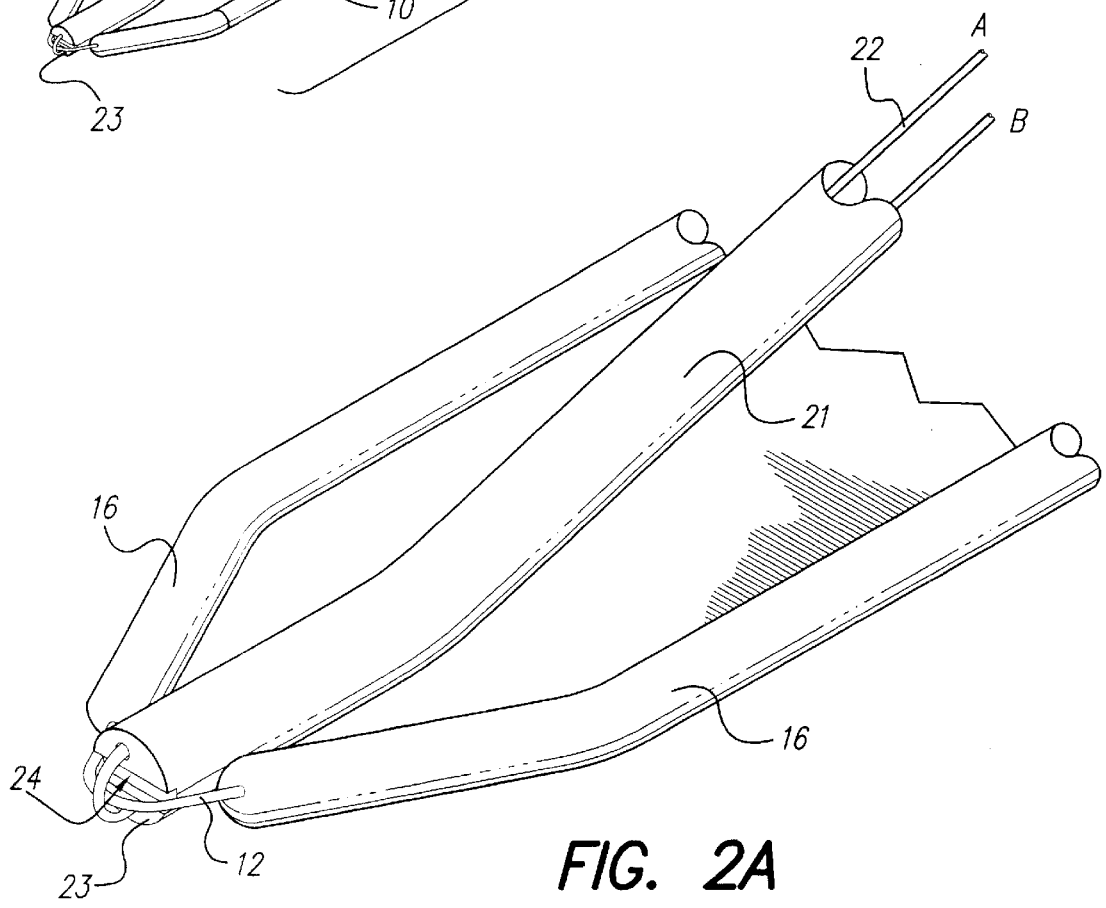
FIG. 2A depicts the manner in which the distal tip of the electrode array of FIG. 1 is held by the distal tip of the insertion stylet of FIG. 2 during the implantation process.
Figure 2B:
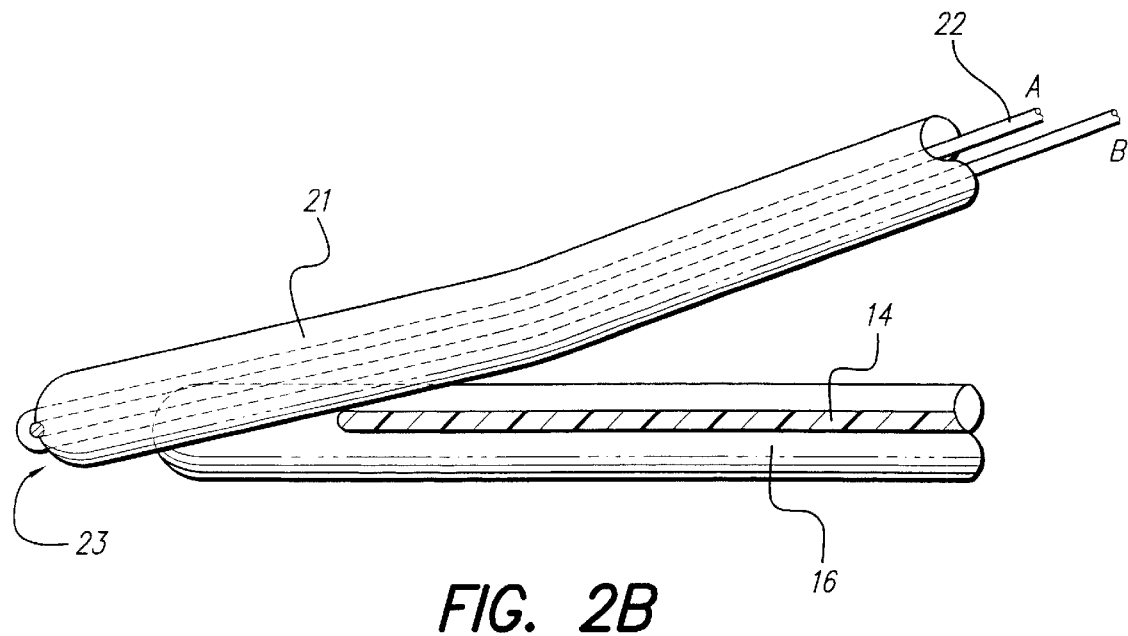
FIG. 2B is a side schematic diagram that illustrates the manner in which a releasable holding string may be threaded through the insertion stylet in order to hold the distal tip of the electrode array in a desired position within a groove of the insertion stylet during the implantation process.

The electrode array 10 of one embodiment includes an insertion stylet 20, as shown in FIG. 2, 2A and 2B, which insertion stylet 20 is made from a tube 21 and holding string 22. A distal tip 23 of the insertion stylet 20 may include a groove or slot 24 into which the memory element 12 may be inserted at the attachment loop 13 of the array 10. The string 22 is threaded through the tube 21 to the distal tip 23, where it wraps around (½ turn) the memory element 12, and is then threaded back through the tube 21. Thus, the two ends of the string 22, labeled "A" and "B" in the figures, exit from the proximal end of the tube 21. The diameter of the tube 21 is typically about the same as the diameter of the cylindrical edge portions 16 of the array 10, e.g., about 1.2 mm.

Figure 3A:
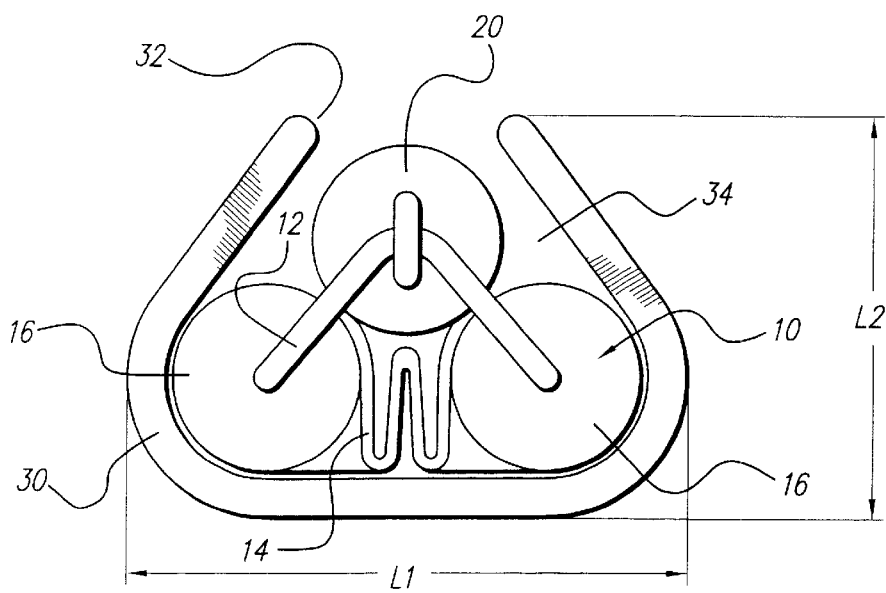
FIG. 3A depicts the manner in which the folded electrode array and insertion stylet fit within the lumen of the needle of FIG. 3.
Figure 3:
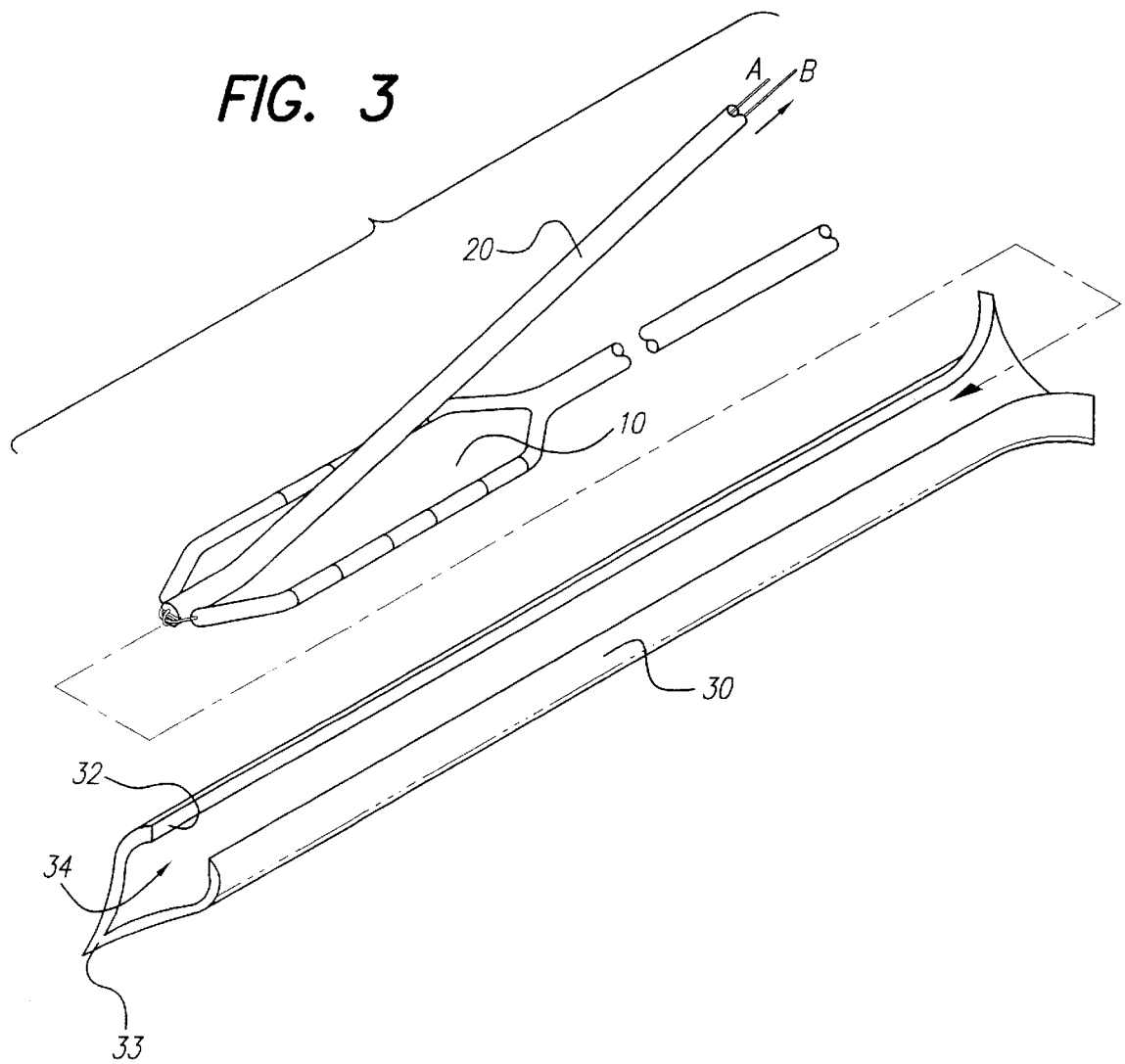
FIG. 3 shows a slitted insertion needle into which the foldable electrode array of FIG. 1 and the insertion stylet of FIG. 2 may be placed.

In order to implant the electrode array 10 with the insertion stylet 20, both the electrode array 10 and insertion stylet 20 are placed within an insertion tool, such as a needle 30, as shown in FIGS. 3 and 3A. The needle 30 preferably has a longitudinal slit 32 that opens up one side thereof along its entire length. The needle 30 preferably has a sharp distal tip 33 to facilitate its insertion into living tissue. The needle 30 is hollow, having a lumen 34 (or open channel) in the center thereof. The electrode 10 and insertion stylet 20 are configured (folded or compressed) to fit within this lumen 34, as illustrated in FIG. 3A. During this configuration (folding) process, the thin membrane 14 folds against itself so that the two perimeter edge portions 16 of the array 10 and the insertion stylet 20 are all held in close proximity to each other.

The needle 30 has approximate dimensions of L1 by L2 (e.g., 4.0 mm by 3.0 mm), as shown in FIG. 3A, or preferably smaller, so it is insertable in between vertebral elements. The needle can have a slit, as shown in FIG. 3A, although it is not necessary as seen in additional needle configurations herein. When included, the slit 32 preferably has a width of about 1.2 mm, the width of the cylindrical edge portions 16 of the lead 10, and also the width of the tube 21 that forms part of the insertion stylet 20. As described in more detail presently, during needle insertion, a removable core stylet is preferably provided in the lumen of the needle which is removed prior to inserting the electrode array.

In order to implant the electrode array, according to one embodiment, the electrode array 10, guided by insertion stylet 20, is inserted into needle 30. The insertion stylet 20 is pushed to eject the electrode array 10 from the lumen 34 of the needle 30 into, e.g., the spinal cord cavity. Once ejected from the lumen of the needle in this manner, the memory element 12 (FIG. 1) deploys the electrode paddle array 10 from its folded position, as shown in FIG. 3A to its substantially flat paddle shape, as shown in FIG. 1.

Once thus deployed, the insertion stylet 20 may be further pushed, and/or the electrode lead 10 may be pulled, so as to manipulate the electrode array within the spinal cord cavity to rest in an optimum or desired position. The needle 30 is then removed from the body, and the electrode lead is released either through the opening at the distal end of the needle or through the slot or slit 32 in the needle. The string 22 is then pulled from either the "A" or "B" end in order to release the electrode array 10 from the insertion stylet 20. The insertion stylet 20 is then also pulled out of the tissue.

Figure 7B:
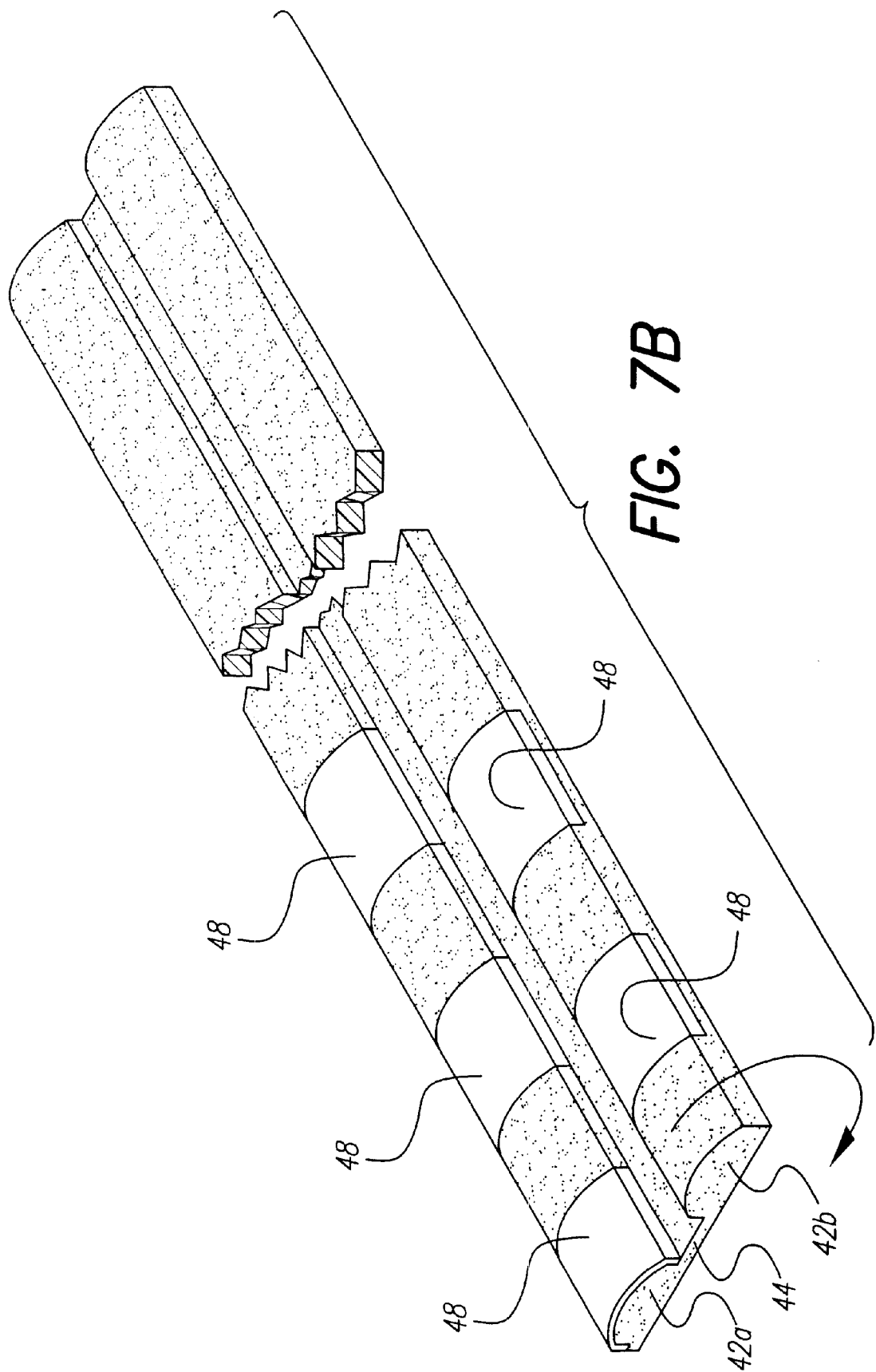
FIG. 7B shows an alternative implantable, foldable electrode array, and a manner of folding the array to fit within the lumen of an insertion tool.

An alternative embodiment of a percutaneously implanted lead/electrode array 40 and percutaneous implant tools made in accordance with the present invention are depicted in the remaining figures. In accordance with such alternative embodiment, there are two or more columns 42 of spaced-apart electrode contacts connected together with a thin webbing 44. In some embodiments, columns 42 and webbing 44 taper into a single lead cable 46, and in other embodiments, the substrate of columns 42 and/or webbing 44 is continuous for the length of the lead (as best seen in FIG. 7B).

In FIG. 4, an embodiment with three columns, 42a, 42b and 42c, is shown. Each column of spaced-apart electrodes comprises a finger substrate made, e.g., from a suitable flexible non-conductive material such as silicone or other implantable lead materials, as is known in the art and discussed in more detail presently. Each finger substrate has a plurality of electrode contacts 48 exposed on the surface hereof. Each electrode contact 48 is, in turn, connected electrically with a wire (not shown) embedded within the column 42 and lead cable 46, thereby facilitating making electrical connection with each electrode. Any suitable implantable conductive material may be used for the electrode contacts 48.

In one particular embodiment of the electrode array 40, each electrode contact has a length of about 2 mm, and each finger of the array has an active length (where the active length is the length from the most proximal electrode contact to the most distal electrode contact) of about 10 mm. The webbing 44 has a thickness of about 0.2 mm, and is made, e.g., from a suitable flexible non-conductive material such as silicone or other implantable lead materials, as is known in the art. Each finger has a cross section having a width of about 1.75 mm and a height of about 0.80 mm. The width of the webbing 44 between adjacent fingers is approximately 0.75 mm.

In order to implant the electrode array 40, the array 40 is inserted into an insertion tool 50 as shown in FIGS. 5 and 6. As the array 40 is inserted into the insertion tool 50, the fingers 42a, 42b and 42c (or however many columns or fingers there are) collapse and fold over each other. The fingers or columns 42 may be tapered so that a distal end is somewhat smaller than the proximal end.

The electrode contacts 48 on the surface of each finger 42 are preferably offset from the location of electrode contacts of an adjacent finger or column. Such offsetting of the electrode contacts facilitates the folding of one column before the next. The electrode array 40 of FIG. 5 in its folded state is shown within the insertion tool 50 in FIG. 6. An electrode array 40 of the present embodiment with two columns 42a and 42b of spaced-apart electrode contacts 48 is shown in FIG. 7A. An additional alternative configuration of an electrode array 40 of the present embodiment is shown in FIG. 7B. As mentioned earlier, the substrate of columns 42 and webbing 44 is continuous for the length of the lead of FIG. 7B. This same configuration, with continuous columns, may be used rather than tapered columns and cable 46 for any of the alternatives described herein. FIG. 7C shows the electrode array of FIG. 7A or FIG. 7B within insertion tool 50.

As array 40 is deployed, it returns to the substantially flat state, as shown in FIGS. 4 and 7B, by virtue of the material(s) and/or formation process(es) used to create array 40. A preferred formation method is injection molding, although other methods, such as other molding methods, casting, or other known methods may be used. A preferred material(s) has good elastic deformation properties, such that, after temporary deformation, the material returns, or substantially returns, to its original shape. Preferred materials include polyurethane and more preferably silicone or some mixture of polyurethane and silicone, or other non-conductive biocompatible materials with good elastic deformation. Array 40 (e.g., of FIG. 7B) is preferably stiff enough to be deployed from insertion tool 50 into position, e.g., in the spinal cord cavity, by pushing its proximal end, which protrudes from the proximal end of insertion tool 50.

Figure 8B:
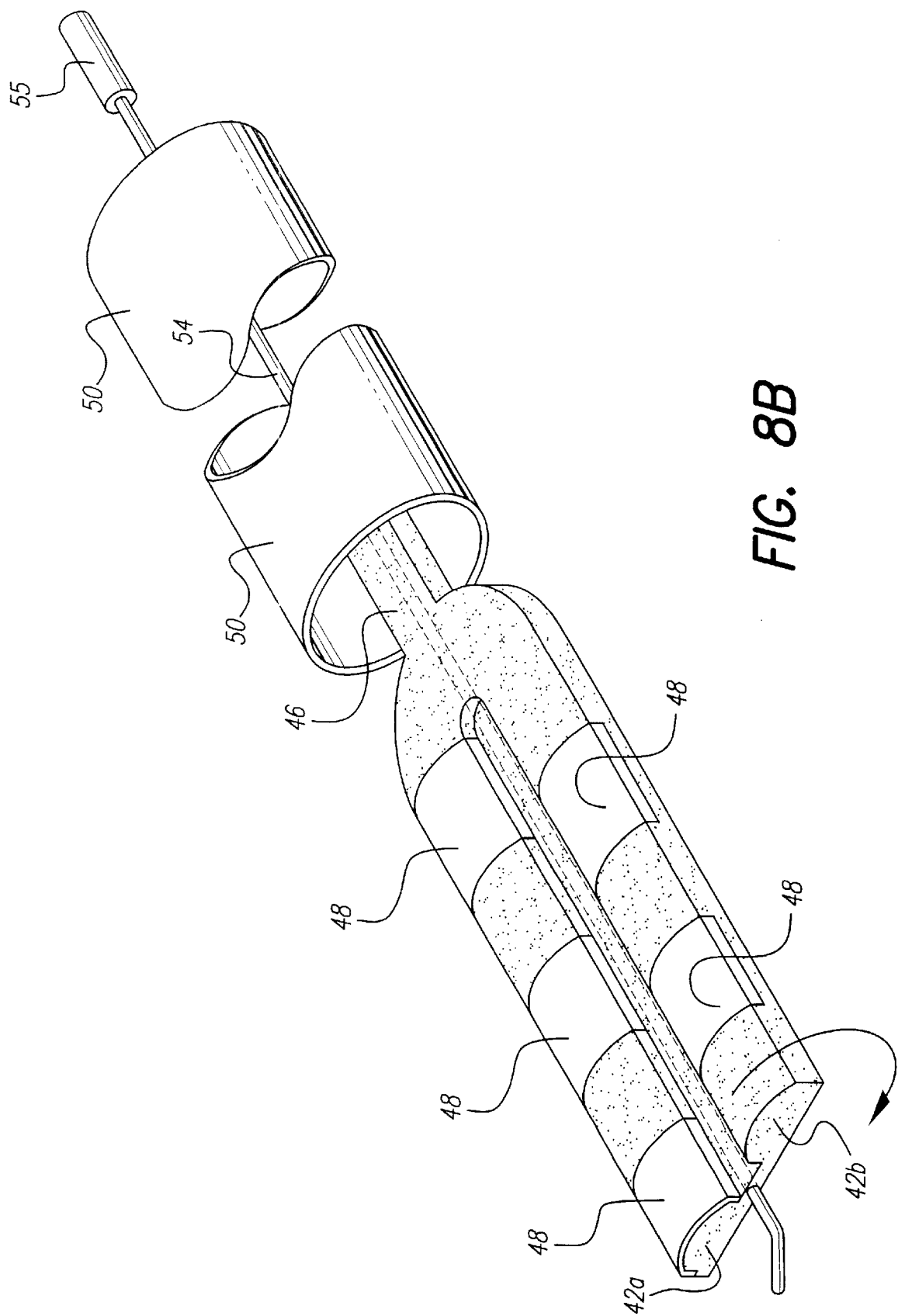
FIG. 8B illustrates the implantable, foldable electrode array of FIG. 8A, with a stylet inserted in the lumen of the electrode array.

In one alternative, a lumen 52 for a steering stylet 54 may be provided through lead cable 46 and through webbing 44, as depicted in FIGS. 8A and 8B, or rather than going through webbing 44, may replace webbing 44. Electrode array 40 is preferably folded into insertion tool 50 as shown in either FIGS. 8A, 8B, and 8C or as in FIGS. 8D and 8E. Insertion tool 50 may be a hollow cylinder or tube that is oblong in cross-section with a width greater than a height (FIGS. 8A, 8B, 8C), similar to the needle 30 insertion tool, may be oblong with a height greater than a width (FIGS. 8D, 8E), or may be circular in cross-section, as in FIG. 7B. For instance, insertion tool 50 may have a width of approximately 3.0 mm and a height of approximately 1.5 mm. The smaller the dimensions of the insertion tools, the better, as this reduces trauma. However, the height and/or width of insertion tool 50 may be as large as about 10 mm to accommodate an electrode array that is as large as about 10 mm. In addition, insertion tool 50 may have a pointed distal tip as in FIG. 3, or distal tips as shown in FIGS. 11A, 11B, 13, and 14, or may have any other useful distal tip configuration.

As shown in FIG. 8C, steering stylet 54 preferably protrudes through the distal end of electrode array 40. Steering stylet 54 preferably has a slightly bent tip, also shown in FIG. 9C, which aids in driving electrode array 40 into position as the bent tip turns while steering stylet handle 55 is rotated. However, steering stylet 54 may, for instance, be straight, and may not protrude from the end of array 40 if there is no opening 56 at the distal end of lumen 52. For example, in yet another alternative (not shown), a lumen for a steering stylet may be provided through lead cable 46 and/or if desired through a column 42 of electrode array 40. Steering stylet 54 is preferably made of a stiff biocompatible material, and more preferably of a biocompatible metal material, such as stainless steel, which is strong enough to guide the insertion process, but flexible enough to allow the steering stylet to be withdrawn from electrode array 40, even if there is a slight bend at the distal tip of the stylet.

Figures 9A, 9B:
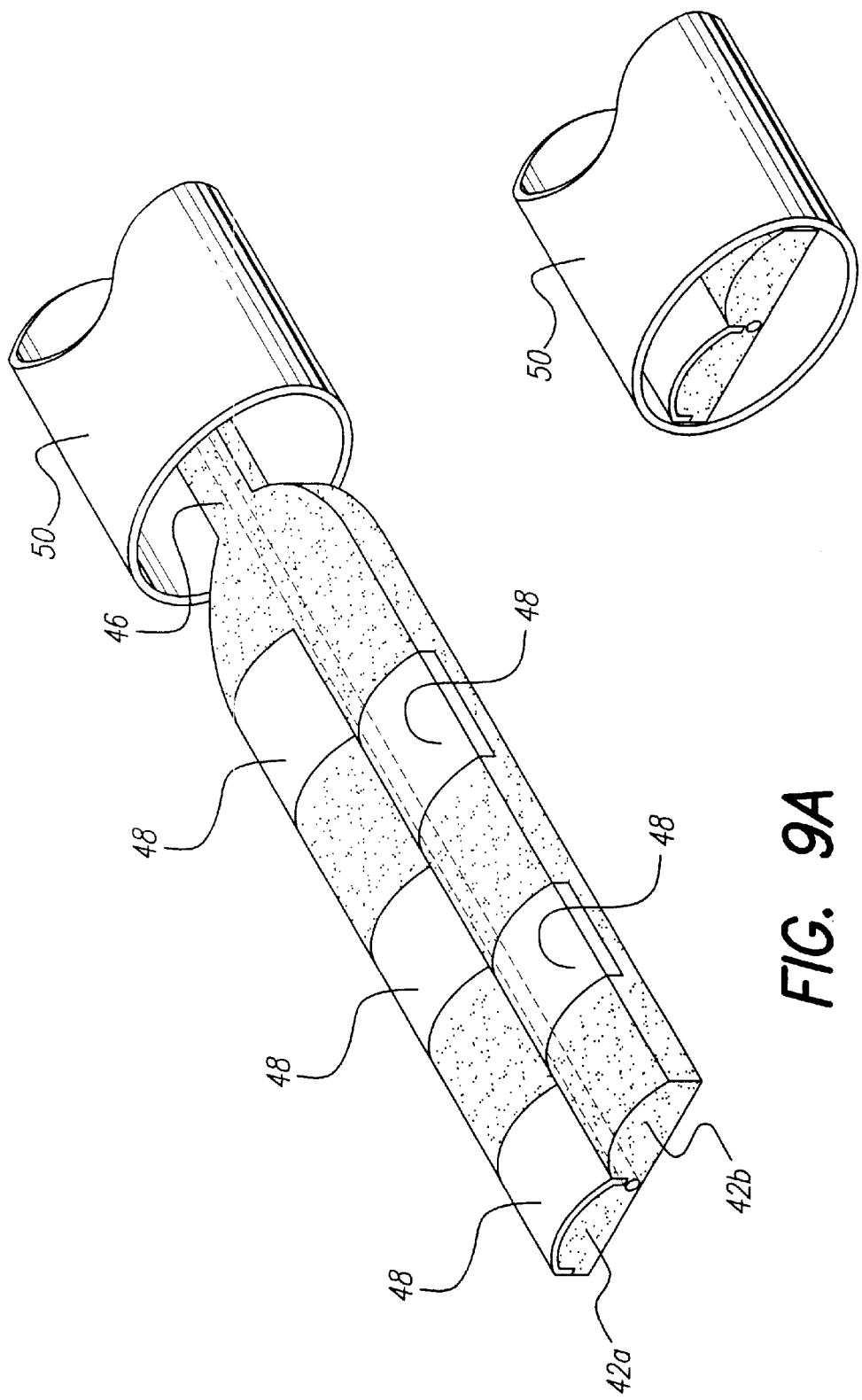
FIG. 9A shows yet another alternative implantable electrode array including a lumen for a stylet, and a manner of inserting the array within the lumen of an insertion tool.
FIG. 9B illustrates the electrode array of FIG. 9A inside the lumen of an insertion tool.

In another alternative, the lumen 52 for steering stylet 54 is provided as shown in FIGS. 9A and 9B. The electrode array 40 of this example is advantageously compact enough, with webbing 44 so reduced or removed, to slide within insertion tool 50 without being folded. Of course, folding the electrode array of this example is still an option, in which case it may be preferable to use an insertion tool with a different cross-sectional shape.

Figure 10:
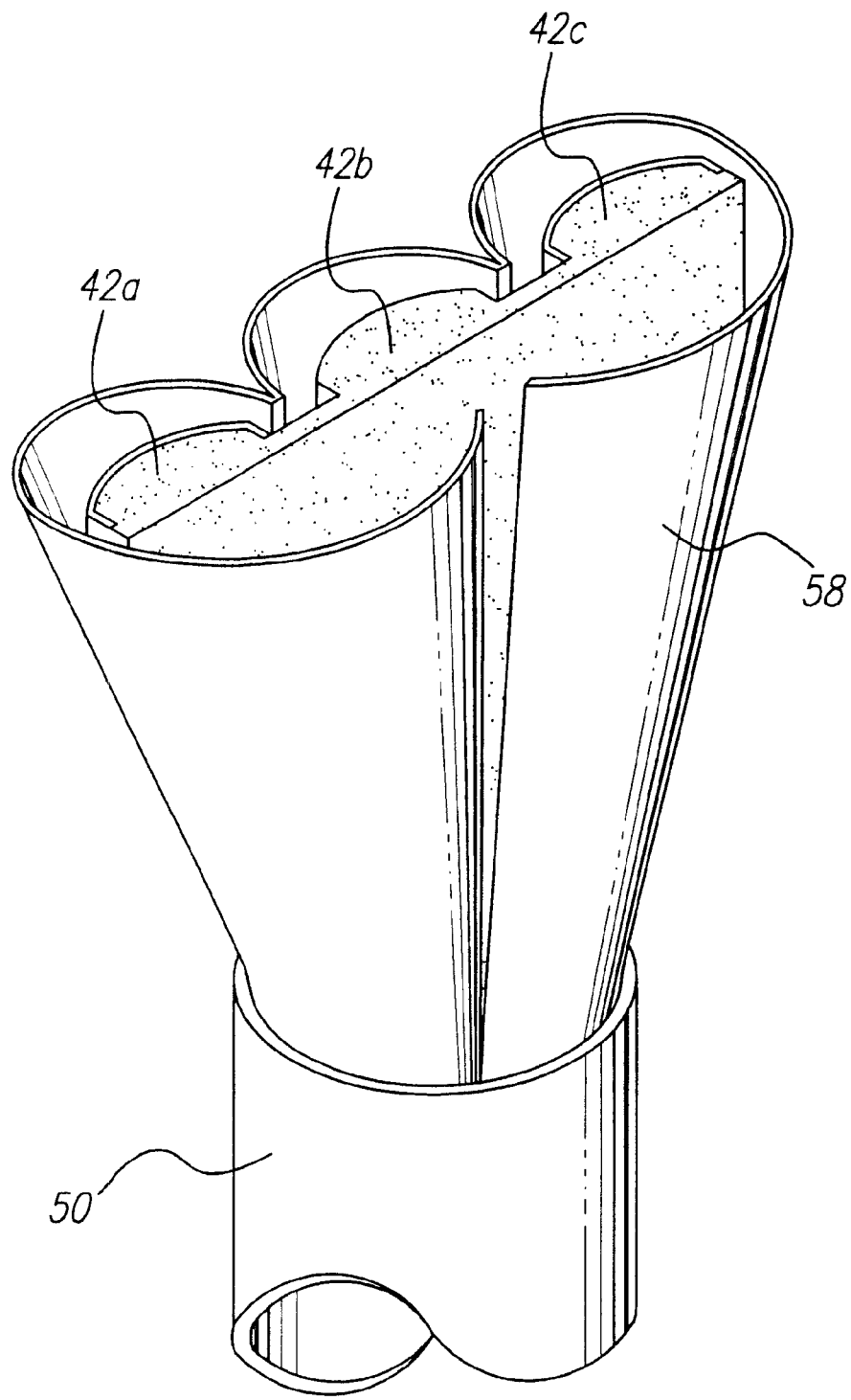
FIG. 10 depicts a loading tool that may be used in conjunction with the insertion tool in order to facilitate the folding and insertion of the electrode array of FIG. 4 into the lumen of an insertion tool.

For some implantations, it may be helpful to employ a loading tool 58, which may, for instance, be shaped as a funnel as illustrated in FIG. 10. With such loading tool 58, which preferably attaches to one end of the insertion tool 50, the lead cable 46 is first inserted through the loading tool 58 and insertion tool 50, and as this lead cable 46 is pulled through the insertion tool 50, the e.g., funnel shape of the loading tool 58 automatically causes the various fingers or columns 42a, 42b, 42c to collapse and fold over each other as they are pulled into the insertion tool 50. Other shapes of loading tool 58 are possible, such as a simple tube, a cone, or other useful shape. In one alternative, the insertion tool 50 is also used as the loading tool 58.

Figure 13:
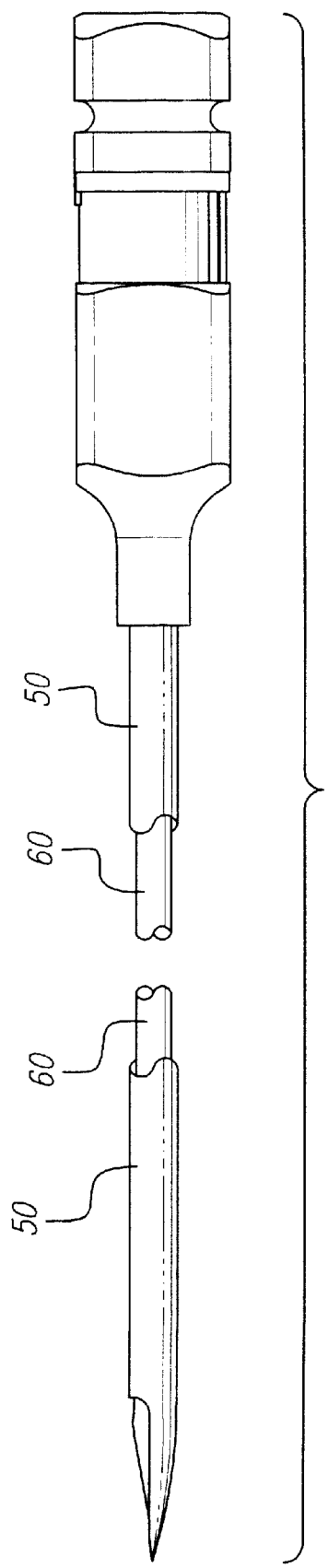
FIG. 13 depicts a side view of the stylet of FIGS. 12A and 12B inserted into the insertion tool of FIGS. 11A and 11B.
Figure 14:
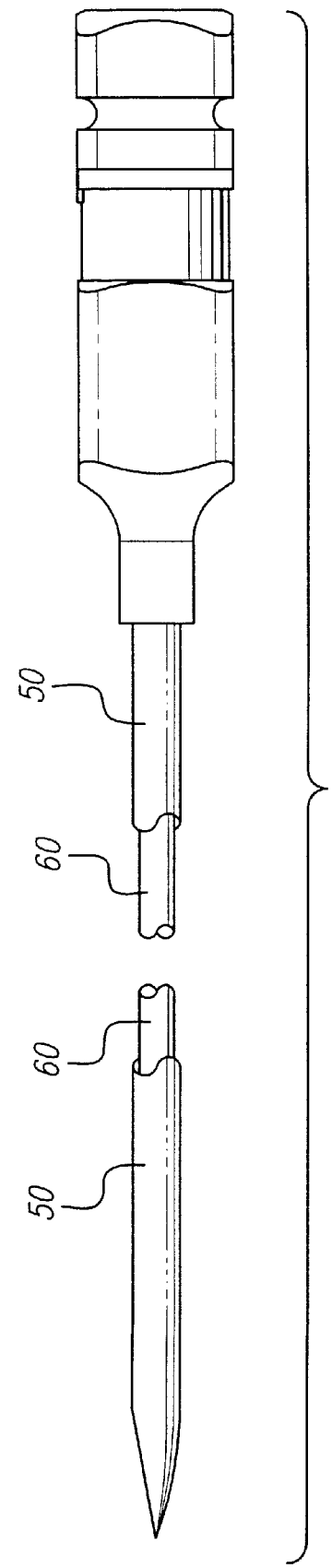
FIG. 14 depicts a side view of an alternative stylet and insertion tool.

As mentioned earlier, the distal tip of insertion tool 50 may be pointed, or may have any other useful configuration. FIGS. 11A and 11B depict an example of an insertion tool 50 useful with the electrode arrays of the current invention. As is known in the art, when an insertion tool 50 (often simply called a needle) is inserted into tissue, a core stylet 60 (FIGS. 12A and 12B) is typically provided within tool 50 to prevent tissue from entering the lumen of the tool (often called 'coring'). FIG. 13 shows the core stylet 60 of FIGS. 12A and 12B inserted in insertion tool 50 of FIGS. 11A and 11B. Once tool 50 is inserted into position, core stylet 60 is removed so that an electrode array, such as electrode array 10 or electrode array 40, may be inserted through insertion tool 50. As is known in the art, a slight upward curve at the distal end of the insertion tool is useful for directing the electrode array as it exits the distal end of insertion tool 50. Another design of insertion tool 50 and core stylet 60 useful with the electrode arrays of the present invention is shown in FIG. 14.

As described above, it is thus seen that the present invention provides a foldable, paddle-type electrode which can be implanted using a simple, needle-type tool without major surgical intervention.

As further described above, it is seen that the invention provides a loading tool that assists with the folding and inserting of the paddle-type electrode into an insertion tool.

While the invention herein disclosed has been described by means of specific embodiments and applications thereof, numerous modifications and variations could be made thereto by those skilled in the art without departing from the scope of the invention set forth in the claims.

What is claimed is:

1. An implantable electrode array comprising:
   a compliant biocompatible substrate configured as two columns, the substrate substantially following the outer edge of a paddle shape;
   a plurality of electrode contacts carried on the substrate;
   conductive wires within the substrate for making electrical contact with each of the plurality of electrode contacts; and
   a shape memory element integral with the substrate;
   whereby the electrode array is foldable to assume a small cross-sectional area during implantation, but whereby the electrode array unfolds to assume an expanded configuration as controlled by the shape memory element after implantation.

2. The implantable electrode array of claim 1 further comprising a flexible membrane formed inside the area formed by the substantially paddle shaped substrate.

3. The implantable electrode array of claim 1 wherein the shape memory element comprises a wire made from at least one of metal and polymer.

4. An implantable electrode array comprising:
   a compliant biocompatible substrate having a width greater than a height;
   a plurality of electrode contacts carried on the substrate;
   conductive wires within the substrate for making electrical contact with each of the plurality of electrode contacts;
   a lumen within the compliant biocompatible substrate, which lumen accepts a stylet for steering the electrode array during implantation;
   whereby the electrode array is foldable to assume a small cross-sectional area during implantation, but whereby the electrode array unfolds to assume an expanded configuration as controlled by the shape of the compliant biocompatible substrate after implantation.

5. The implantable electrode array of claim 4 wherein the lumen within the substrate extends through the substrate to an opening at a distal end of the electrode array.

6. The implantable electrode array of claim 4 wherein the lumen within the substrate extends substantially through the substrate.

7. The implantable electrode array of claim 4 wherein the substrate is foldable along an axis substantially parallel to the substantially parallel columns, said axis lying in the region of the flexible substrate between the columns of electrodes.

8. The implantable electrode array of claim 4 wherein the plurality of electrodes are spaced-apart in at least two substantially parallel columns.

9. The implantable electrode array of claim 8 wherein the number of substantially parallel columns of spaced-apart electrodes comprises three.

10. The implantable electrode array of claim 4 wherein the flexible substrate has a width of between about 6.5 and 7.0 mm and a length of about 8–12 mm, and wherein each column of electrodes has a height of between about 0.6 and 1.0 mm, and wherein the flexible substrate has a height in the region between the electrode columns of approximately 0.10 to 0.30 mm.

11. A system for implanting an expandable electrode array comprising:
 an electrode array, the electrode array comprising:
 a compliant biocompatible substrate;
 a plurality of electrodes integral with a surface of the substrate; and
 conductive wires for making electrical contact with each electrode in the plurality of electrodes;
 the flexible substrate normally assuming a substantially flat shape, but being collapsible so as to configure the electrode array in a folded or compressed state; and
 an insertion tool configured to facilitate implantation of the electrode array into living tissue while the electrode array is still in a folded or compressed state.

12. The system of claim 11 wherein the plurality of electrodes are spaced-apart in at least two substantially parallel columns.

13. The system of claim 12 wherein the number of substantially parallel columns of spaced-apart electrodes comprises three.

14. The system of claim 11 wherein the insertion tool comprises a hollow cylinder wherein the folded or compressed electrode array may be inserted and a distal tip configured to allow expulsion of the electrode array into living tissue, wherein the cylinder is oblong in cross-section.

15. The system of claim 14 further comprising a removable core stylet insertable into the lumen of the cylinder, which stylet has an oblong cross-section similar to the dimensions of the lumen.

16. The system of claim 11 further comprising a loading tool detachably connected to a proximal end of the insertion tool, the loading tool having a shape that facilitates configuring the electrode array in its folded or compressed state from its substantially flat state as such electrode array is longitudinally inserted into the insertion tool.

17. A system for implanting a foldable or compact electrode array comprising:
 a foldable or compact electrode array, the electrode array comprising;
 a compliant biocompatible substrate;
 a plurality of electrodes integral with a surface of the substrate; and
 conductive wires for making electrical contact with each electrode in the plurality of electrodes; and
 an insertion tool configured to facilitate implantation of the electrode array into living tissue, the insertion tool comprising:
 a cylinder defining a lumen for accepting the foldable or compact electrode array; and
 a distal tip configured to allow expulsion of the electrode array into living tissue;
 wherein the cylinder is oblong in cross-section.

18. The system of claim 17 further comprising a removable core stylet insertable into the lumen of the cylinder, which stylet has an oblong cross-section similar to the dimensions of the lumen.

19. The system of claim 17 further comprising a loading tool detachably connected to a proximal end of the insertion tool, the loading tool having a shape that facilitates configuring the electrode array in its folded or compressed state from its substantially flat state as such electrode array is longitudinally inserted into the insertion tool.

20. A method of implanting an expandable electrode array through the lumen of a needle, comprising:
 forming an electrode array having a plurality of substantially parallel columns of spaced apart electrodes on a flexible substrate and a lumen within the substrate configured to accept a steering stylet;
 providing a needle having a lumen therethrough and a distal tip configured to allow expulsion of the electrode array into living tissue;
 providing a removable core stylet insertable into the lumen of the needle;
 inserting the core stylet into the lumen of the needle;
 injecting the needle into living tissue;
 removing the core stylet from the lumen of the needle;
 inserting the steering stylet into the lumen of the electrode array;
 folding the columns of electrodes against each other;
 inserting the folded columns into the lumen of the needle;
 using the steering stylet to expel the folded columns of electrodes from the lumen of the needle into the living tissue; and
 unfolding the columns of electrodes to form a paddle-type array of substantially parallel columns of electrodes.

21. The method of claim 20 wherein the needle is oblong in cross-section.

22. The method of claim 20 further comprising providing a loading tool detachably connected to a proximal end of the needle, the loading tool having a shape that facilitates folding the columns of electrodes against each other, and wherein folding the columns of electrodes against each other and inserting the folded columns into the lumen of the needle comprise inserting the electrode array through the loading tool and into the needle.

23. A method of implanting a foldable or compact electrode array through the lumen of a needle, composing:
 forming an electrode array having a plurality of substantially parallel columns of spaced apart electrodes on a flexible substrate;
 providing a needle having an oblong lumen therethrough and a distal tip configured to allow expulsion of the electrode array into living tissue;
 providing a removable core stylet insertable into the lumen of the needle;
 inserting the core stylet into the lumen of the needle;
 injecting the needle containing the core stylet into living tissue;
 removing the core stylet from the lumen of the needle;
 inserting the electrode array into the lumen of the needle;
 expelling the electrode array into the living tissue.

24. The method of claim 23 wherein the electrode array includes a lumen within the substrate configured to accept a steering stylet, and further comprising inserting the steering stylet into the lumen of the electrode array and using the steering stylet to expel the electrode array from the lumen of the needle into the living tissue.

* * * * *